United States Patent [19]
Kensey

[11] Patent Number: 5,391,143
[45] Date of Patent: Feb. 21, 1995

[54] METHOD AND SYSTEM FOR EFFECTING WEIGHT REDUCTION OF LIVING BEINGS

[75] Inventor: Kenneth Kensey, Chester Springs, Pa.

[73] Assignee: Kensey Nash Corporation, Exton, Pa.

[21] Appl. No.: 31,005

[22] Filed: Mar. 12, 1993

[51] Int. Cl.⁶ .............................................. A61M 37/00
[52] U.S. Cl. ........................................... 604/5; 604/28
[58] Field of Search ......................... 604/5, 28, 29, 30

[56] References Cited

U.S. PATENT DOCUMENTS 3,929,130 12/1975 Hargest .................................... 604/5
4,612,007 9/1986 Edelson ................................. 604/28

FOREIGN PATENT DOCUMENTS 2581546 11/1986 France .

Primary Examiner—Jerome L. Kruter
Attorney, Agent, or Firm—Caesar, Rivise, Bernstein Cohen & Pokotilow, Ltd.

[57] ABSTRACT

Method and systems for separating a first material, e.g., fat, from lymphatic fluid flowing through a duct within the body of a living being, so that the material is removed from the being's body or recirculated. The system comprises a reservoir for receipt of that material, and an elongated conduit implanted within the vascular system and having a distal end in fluid communication with the duct and a proximal end in fluid communication with the reservoir. An implantable pump and/or valve may be provided to effect the operation of the system under control from outside the body of the being.

65 Claims, 5 Drawing Sheets

METHOD AND SYSTEM FOR EFFECTING WEIGHT REDUCTION OF LIVING BEINGS

BACKGROUND OF THE INVENTION

This invention relates generally to medical devices and methods of removing one or more materials from the lymphatic fluid in a living being's body, and more particularly to systems and methods for effecting weight reduction of living beings by removing fat from the lymphatic fluid thereof.

Obesity control is of considerable concern to the medical community, as well as to the public at large, for medical as well as cosmetic reasons. While sensible eating and exercise are deemed to be the best methods for effecting weight loss and maintaining a desired weight, for many persons such techniques are unsuccessful or unavailing.

Thus, a need presently exists for providing systems and methods for controlling obesity.

OBJECTS OF THE INVENTION

Accordingly, it is a general object of this invention to provide systems and methods of use which address that need.

It is another object of this invention to provide systems and methods of use for effecting the removal of one or more predetermined materials found in the lymphatic fluid by draining a portion of that fluid from the beings body.

It is a further object of this invention to provide systems and methods of use for effecting the removal of fat from the body of a being by drainage of a portion of lymphatic fluid from the being's body.

It is a further object of this invention to provide implantable systems and methods of use for effecting the removal of fat or other lymphatic carried components from the body of a being by drainage of a portion of lymphatic fluid from the being's body.

SUMMARY OF THE INVENTION

These and other objects of this invention are achieved by providing methods and systems for removing at least one predetermined material, e.g., fat, from the body of a living by gaining access to a duct through which lymphatic fluid containing the material flow, and withdrawing the lymphatic fluid and the material from the duct.

The system basically comprises reservoir means and first conduit means. The first conduit means, e.g., an elongated flexible catheter, is configured to be located within the body of the being, e.g., is suitable for location within the vascular system, and coupled to a duct having lymphatic fluid flowing therethrough so that said lymphatic fluid flows into the conduit means. The conduit means, e.g., a proximal portion thereof, is coupled to the reservoir means for carrying the lymphatic fluid into said reservoir means. The reservoir means is operable, e.g., utilizes gravity, to cause the first material, e.g., the fat, in the lymphatic fluid to be separated therefrom, whereupon that material can be removed from the body of the being.

In accordance with one preferred embodiment of this invention the system is implantable within the being's body and includes a second conduit and a third conduit. The second conduit is coupled to the reservoir means and to a first internal portion of the body of the being, e.g., the peritoneum, or a portion of the gastro-intestinal tract, or the venous system, or the lung, for carrying the lymphatic fluid remaining after the separation of the first material, e.g., fat, therefrom to that first internal portion for reabsorption thereby. Such action can be carried out continuously or repeatedly at regular or irregular intervals. The third conduit is coupled to the reservoir means and to a second internal portion of the body of the being, e.g., the urinary bladder, for carrying the first material, e.g., fat, after it has been separated from the lymphatic fluid to the second internal portion for excretion thereby.

In accordance with the method of this invention the first conduit is coupled to a duct within the body of the being having lymphatic fluid flowing therethrough so that that fluid flows into and through the first conduit, whereupon the at least one predetermined material, e.g., fat, within the lymphatic fluid is removed from the body of the being continually, i.e., continuously or repeatedly at regular or irregular intervals, over an extended period of time.

BRIEF DESCRIPTION OF THE DRAWING

Other objects and many of the attendant advantages of this invention will be readily appreciated as the same becomes better understood by reference to the following detailed description when considered in connection with the accompanying drawings wherein.

DETAILED DESCRIPTION OF THE PREFERRED EMBODIMENT

Figure 1:
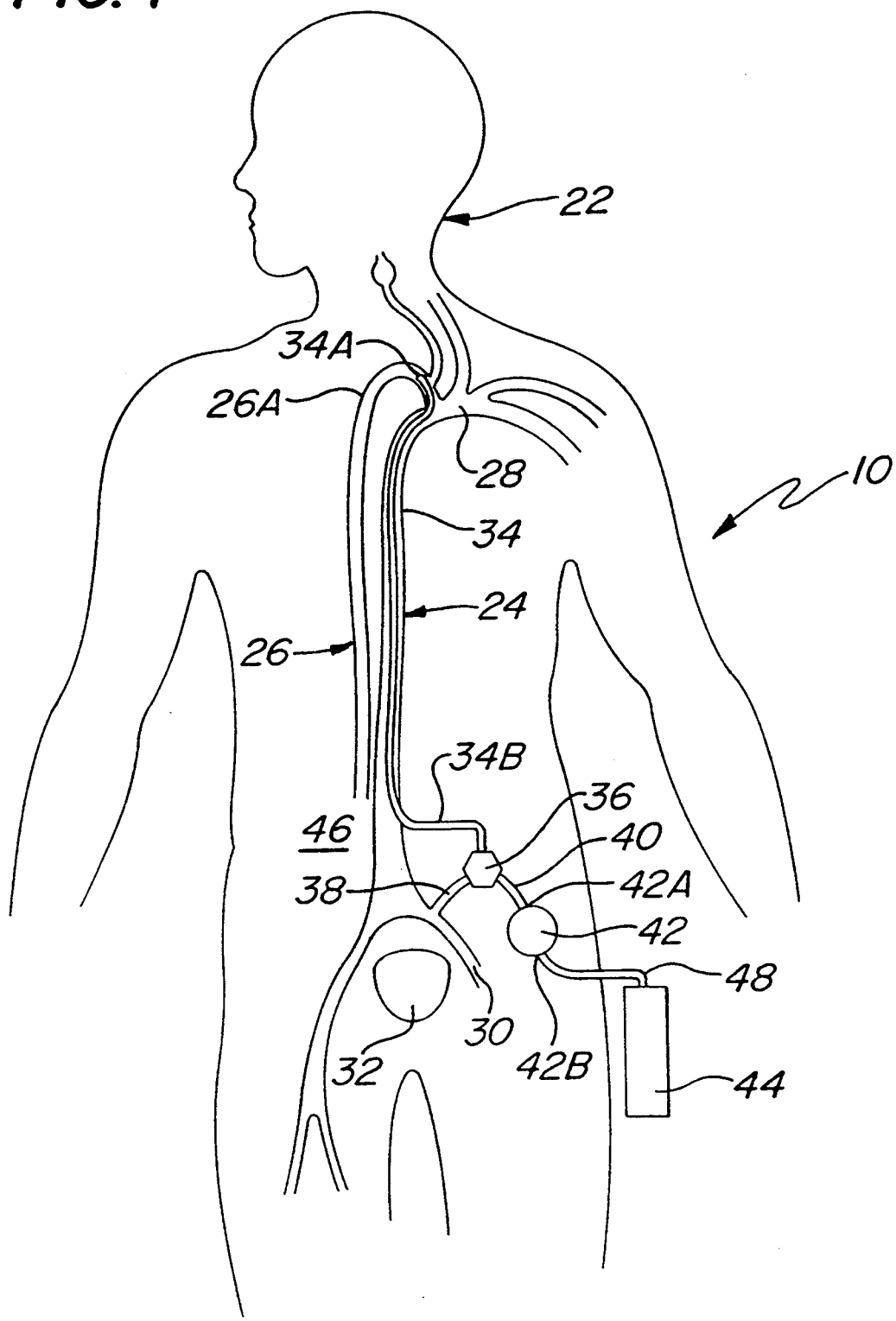
FIG. 1 is a schematic diagram of a portion of the body of a living person showing one embodiment of the system of this invention connected thereto.

Referring now in greater detail to the figures there is shown at 10, 100, 200, 300, and 400 in FIGS. 1-5, respectively, systems constructed in accordance with the teachings of this invention for removing one or more predetermined materials from lymphatic fluid flowing through the body of a living being 22. In accordance with one preferred aspect of this invention, and which will be described in detail hereinafter, the material removed by those systems comprises fat. Accordingly, the systems of this invention are particularly suitable for use as a viable means for weight reduction and obesity control. It should, however, be pointed out that the removal of fat is just one application of the subject invention. Thus, the systems and methods of this invention can be used to effect the removal of one or more other materials, such as T cells, cholesterols, phosphoglycerides, triglycerides, low density lipoproteins, other specific proteins, other specific gamma globulins, electrolytes, and water from the lymphatic fluid for various reasons, e.g., collection, measurement, analysis, treatment, separation, and/or disposal. In fact, the systems and methods of this invention can be used to drain a portion of the lymphatic fluid from the lymphatic system to monitor and/or detect various parameters relating thereto, e.g., to provide data via telemetry, and/or to recirculate the lymphatic fluid or one or more materials contained within the lymphatic fluid back to the being's body. Notwithstanding those various applications of this invention, the remainder of this detailed description will address the construction and usages of the various inventive systems for weight reduction and obesity control.

Before describing such systems a brief description of the portion of the body of the being 22 shown in the various figures is in order. As is known the thoracic duct and the right lymphatic duct usually merge into their associated subclavian veins. Each of the figures of this drawing shows a portion of the being's venous system 24 and the lymphatic system 26 to which the various inventive systems 10–400 are coupled. As should be appreciated by those skilled in the art the anatomic structures shown herein are greatly simplified views, e.g., only the thoracic duct and its associated subclavian vein are shown. The thoracic duct is designated by the reference numeral 26A and its associated subclavian vein by the reference numeral 28. The femoral vein and the urinary bladder are also shown in the various figures and are designated by the reference numerals 30 and 32, respectively. Other anatomical structures which are shown in various specific figures will be identified and discussed later.

The first embodiment of a system constructed in accordance with this invention to be discussed is the system 10 of FIG. 1. That system basically comprises a drainage lumen 34, a reservoir or separator 36, a pair of outlet conduits 38 and 40, a valve/pump assembly 42, and a collector 44. Each system of this invention makes use of a drainage lumen. That lumen can be of any suitable construction for implantation and long-term residence within the body of the being 22, e.g., extending through the venous system or subcutaneously or through some other suitable internal passageway. In the embodiment 10 shown in FIG. 1. the drainage lumen 34 is an elongated conduit formed of a flexible biocompatible material, e.g., a medical grade plastic like used in vascular catheters, having a distal end 34A and a proximal end 34B. The lumen 34 is located within and extends through a portion of the venous system 24 so that its distal end 34A is in fluid communication with the interior of the thoracic duct 28 and its proximal end 34B exits from the venous system in the region of the being's abdomen 46. The proximal end of the lumen 34 is in fluid communication with the reservoir/separator 36. Accordingly, a portion of the lymphatic fluid flowing through the thoracic duct drains into the lumen 34 and is carried through the lumen to the reservoir.

The reservoir/separator 36 is an implantable device, which is implanted in the being at any suitable location, e.g., abdominal area as shown, and the comprises an internal chamber (not shown) into which the drained lymphatic fluid is received. Nonmiscible fat in the lymphatic fluid separates out from the fluid within the reservoir/separator and moves to one portion, e.g., an upper portion, of the chamber, while the remaining lymphatic fluid will, under the influence of gravity reside at another portion, e.g, the bottom, of the chamber. If necessary mechanical and/or chemical means may be provided within the reservoir/separator chamber to effect the separation of miscible fat from the lymphatic fluid, whereupon the separated fat will be located or reside in one portion (e.g., the top) of the chamber, while the remaining lymphatic fluid (i.e., the lymphatic fluid minus the separated fat) will reside in another portion (e.g., the bottom) of the chamber.

The chamber of the reservoir/separator 36 includes a pair of outlet ports in fluid communication with the outlet conduits 40 and 38, respectively, to carry the separated fat and the remaining lymphatic fluid, respectively, out of the separator/reservoir 36. In particular, the outlet port which is in communication with the conduit 38 is in fluid communication with the interior portion of the chamber in which the lymphatic fluid minus the separated fat resides. That conduit is also coupled to and in fluid communication with the femoral vein 30. Accordingly, the lymphatic fluid minus the separated fat flows from the reservoir/separator on to the venous system 24 continuously for reabsorption by the being.

The outlet port which is in communication with the conduit 40 is also in fluid communication with the interior portion of the chamber in which the separated fat resides. That conduit is also coupled to and in fluid communication with the valve/pump assembly 42. The valve/pump assembly is also an implantable device, which can be of any suitable construction for pumping the separated material, e.g., the fat, out of the reservoir/separator 36, under control from outside the body of the being, and includes an inlet port 42A in fluid communication with the conduit 40 and an outlet port 42B in fluid communication with a conduit 48. The conduit 48 is in fluid communication with the collector 44.

In the embodiment system 10 the collector 44 comprises a hollow vessel which, unlike the other components of the system 10, is located outside the being's body. Thus the conduit 40 extends from the implanted valve pump assembly 42 through a percutaneous incision or puncture to the collector 44.

One exemplary valve/pump 42 assembly is a "Peritoneo-Venous Shunt" such as sold by Denver Biomedicals, Inc of Evergreen Colo. That assembly basically includes a squeezable chamber (not shown) and a one way (e.g., duck-bill) valve. The squeezable chamber is coupled to the input port 42A for receipt of the separated fat from the reservoir/separator and is arranged to be manually squeezed, by the application of digital pressure to it through the being's skin, to force the fat through the valve to the outlet port, whereupon it flows into the conduit 48 and from there to the collector. The valve prevents back flow and isolates the system from the ambient surroundings. Other implantable valved pumping devices can be used for the assembly 42. Such other devices may be operated manually (such as by externally applied pressure) or in response to changes in lymphatic fluid parameters, or by external control accomplished electrically, electrostatically, or magnetically by means located outside the being's body so that no access port is necessary through the being's body to effect pump/valve control. Moreover, the valve/pump assembly may be operated under computer control to effect operation a desired times or in response to monitored parameters or patient conditions.

Figure 2:
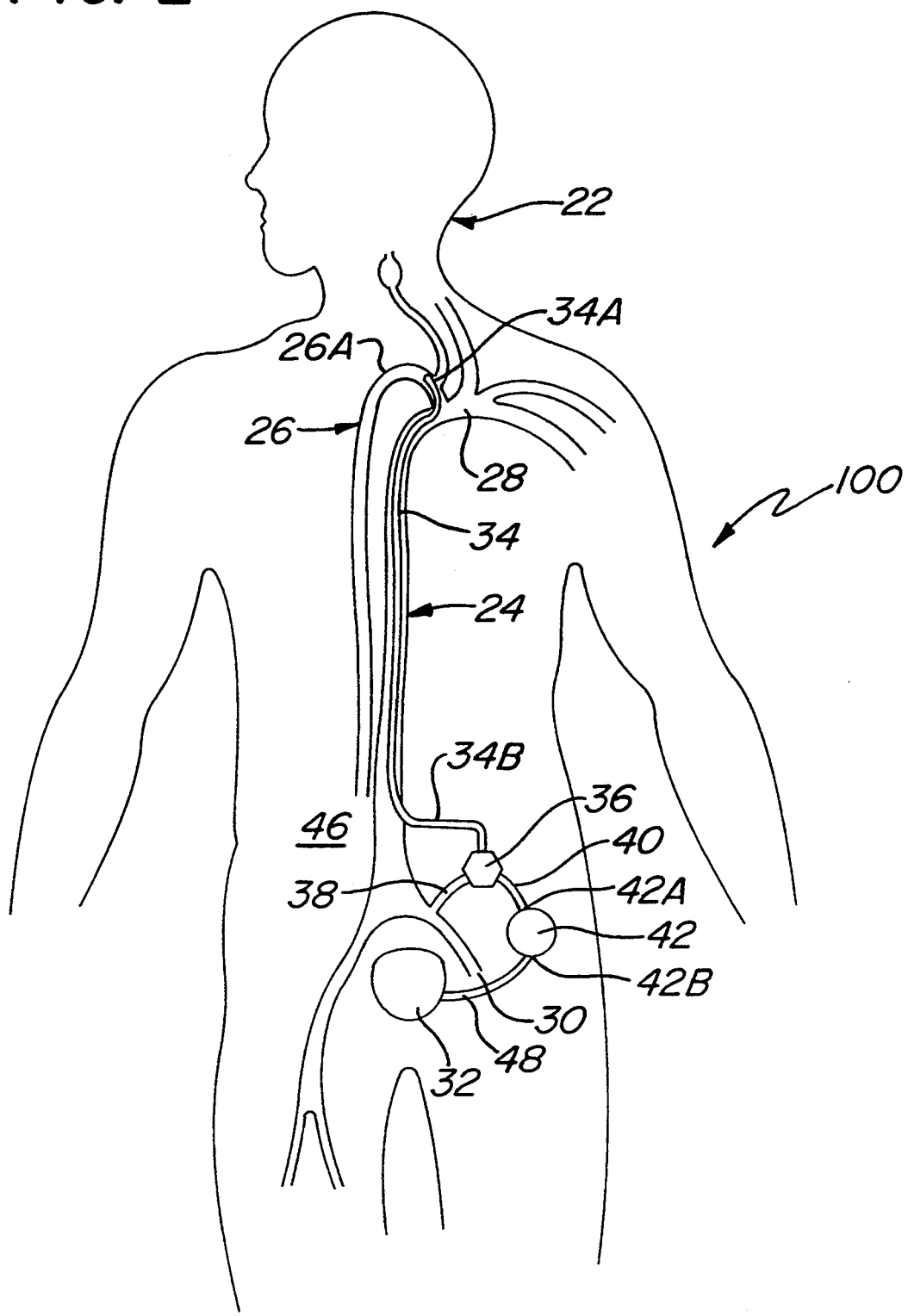
FIG. 2 is a schematic diagram like that of FIG. 1 but showing an alternative embodiment of the system of this invention.

The system 100 shown in FIG. 2 makes use of the being's urinary bladder 32 to excrete or remove the separated fat from his/her body and is identical in construction to the system 10 except that it does not include an external collector vessel 44 for the removed fat as does system 10. In the interest of brevity the components of the system 100 which are the same as those of system 10 will be given the same reference numerals and the details of their construction and operation will not be reiterated. Accordingly, as can be seen the outlet conduit 48 from the reservoir/separator is coupled to and in fluid communication with the being's urinary bladder 32. With such an arrangement the removed fat can be pumped to the urinary bladder when desired, e.g., continuously, periodically, or irregularly, so that the fat will be excreted from the body with urine.

Figure 3:
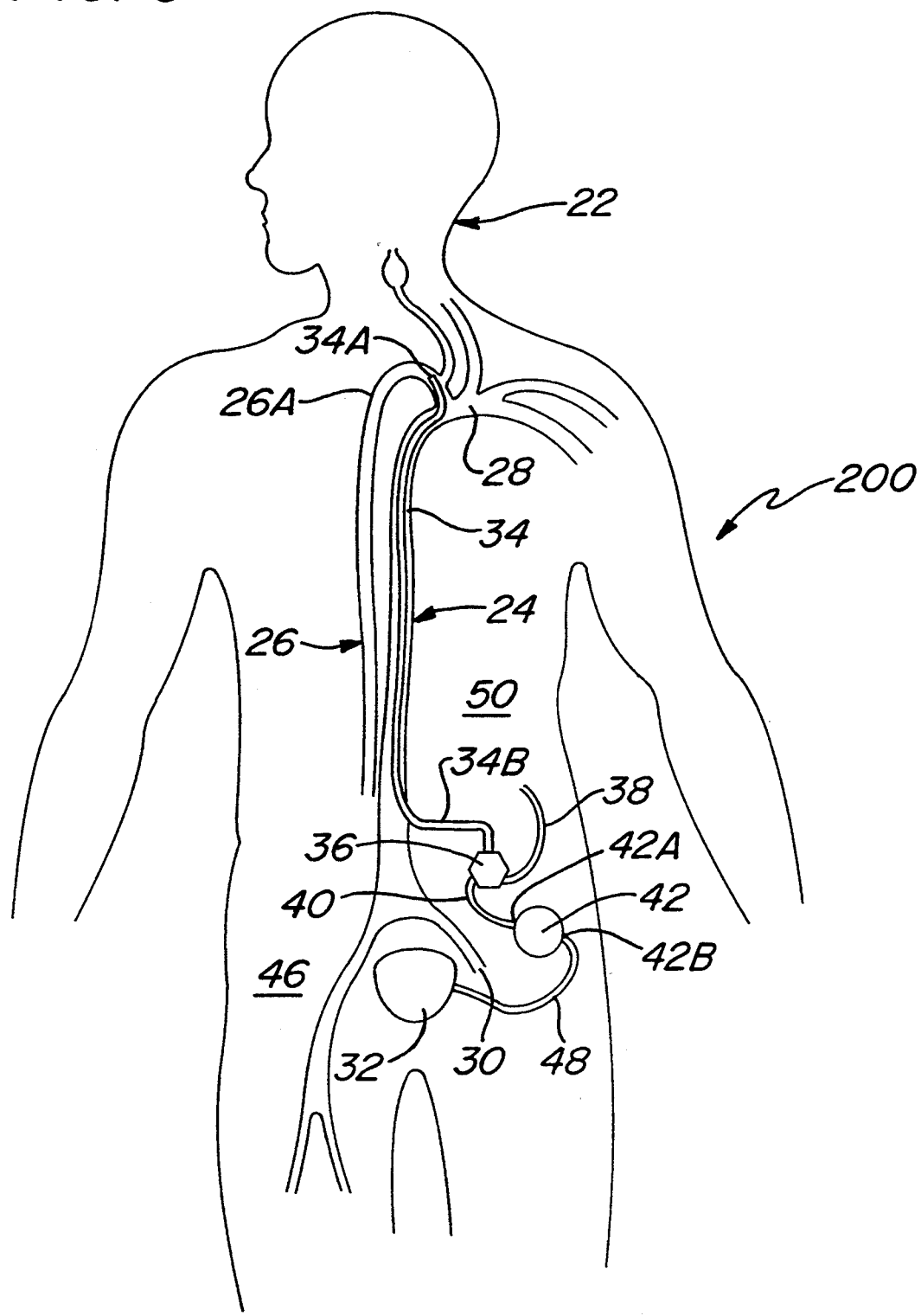
FIG. 3 is a schematic diagram like that of FIG. 1 but showing another alternative embodiment of the system of this invention.

The system 200 shown in FIG. 3 also makes use of the being's urinary bladder 32 to excrete or remove the separated fat from his/her body, and is thus identical in construction to the system 100. However, unlike the system 100 it makes use of the peritoneum 50 for effecting the reabsorption of the lymphatic fluid, whereas system 100 makes use of the venous system 24, e.g., the femoral vein. Since the components of the system 200 are the same as those of the system 100 they are given the same reference numerals and the details of their construction and operation will not be reiterated.

As can be seen in FIG. 3 the outlet conduit 38 from the reservoir/separator is coupled to an in fluid communication with the being's peritoneum 50 so that lymphatic fluid minus the separated fat is continuously provided to the peritoneum for reabsorption.

Figure 4:
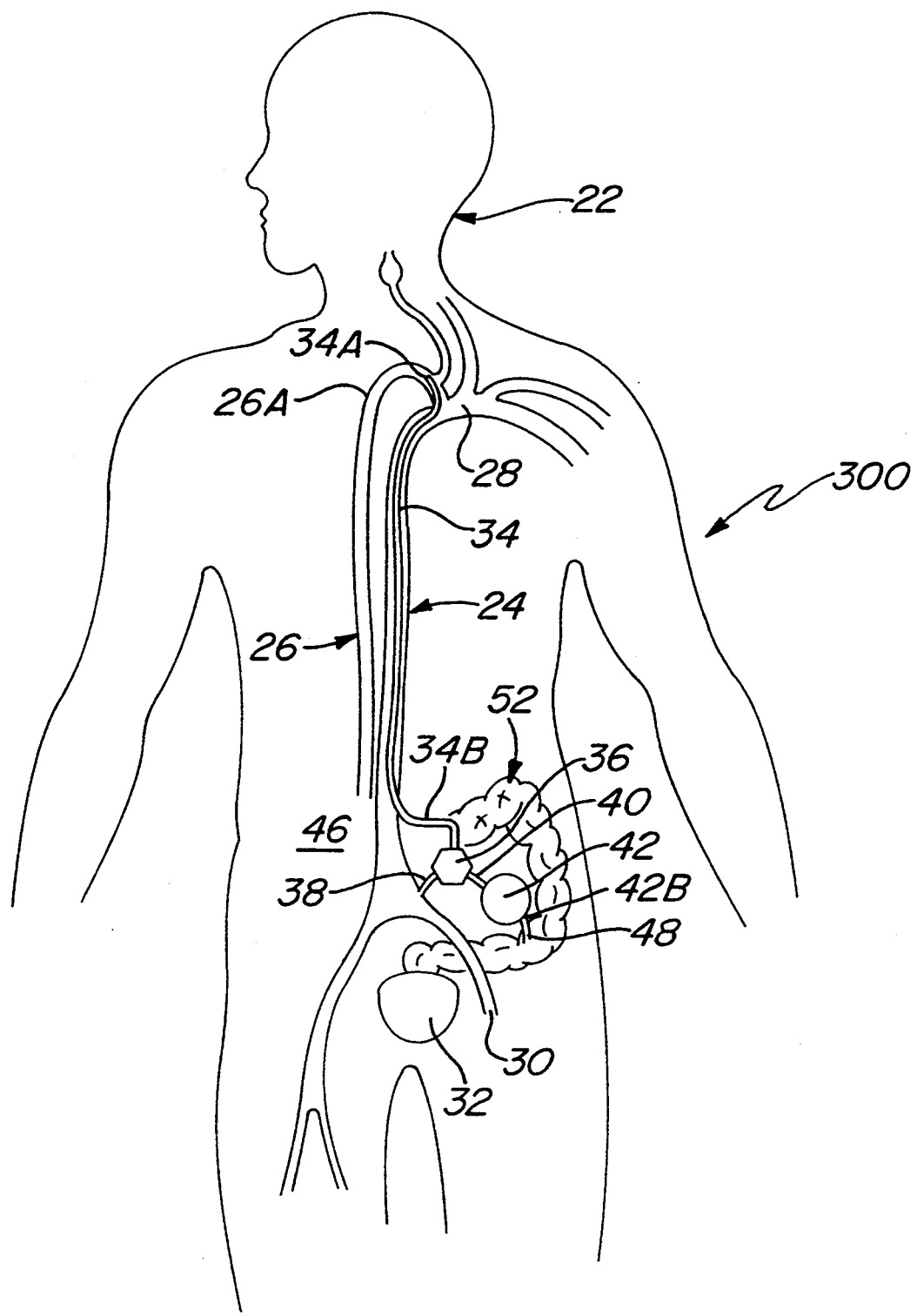
FIG. 4 is a schematic diagram like that of FIG. 1 but showing yet another alternative embodiment of the system of this invention.

The system 300 shown in FIG. 4 is like the embodiment 100 of FIG. 2 in that it makes use of the venous system 24 for reabsorption of the lymphatic fluid minus the removed fat. However, unlike system 100 the system 300 makes use of the being's gastro-intestinal tract, e.g., the bowel 52, to excrete or remove the separated fat from his/her body. The system 300 is identical in construction to the system 100 so that the same components of those systems are given the same reference numerals and the details of their construction and operation will not be reiterated.

As can be seen in FIG. 4 the outlet conduit 48 from the valve/pump assembly 42 is coupled to an in fluid communication with the being's bowel 52. With such an arrangement the removed fat can be pumped to the gastro-intestinal tract, e.g., the bowel, when desired, e.g., continuously, periodically, or irregularly, so that the fat will be excreted from the body with feces. It should be noted that if the material withdrawn from the lymphatic system by this invention, e.g., the fat, is introduced into a suitable upper portion of the gastro-intestinal tract it may be reabsorbed therein, thereby reducing the person's hunger.

Figure 5:
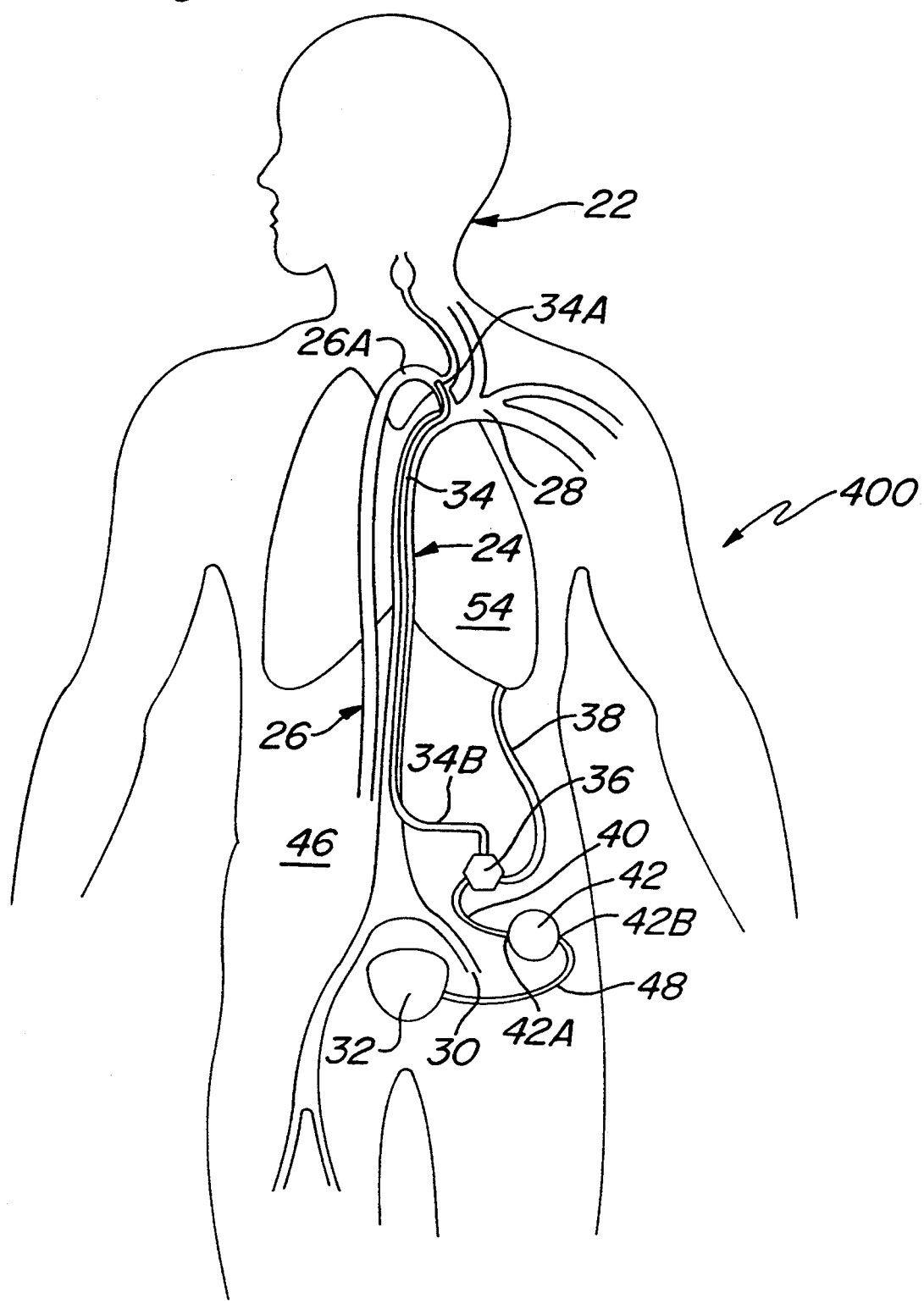
FIG. 5 is a schematic diagram like that of FIG. 1 but showing still another alternative embodiment of the system of this invention.

The system 400 shown in FIG. 5 is identical in construction to the system 200 in FIG. 3 and also makes use of the being's urinary bladder 32 to excrete or remove the separated fat from his/her body. However, the system 400 makes use of the thoracic cavity 54 for effecting the reabsorption of the lymphatic fluid, whereas system 300 makes use of the peritoneum 50. As before since the components of the system 400 are the same as those of system 200 they are given the same reference numerals and the details of their construction and operation will not be reiterated.

As can be seen in FIG. 5 the outlet conduit 38 from the reservoir/separator 36 is coupled to an in fluid communication with the being's thoracic cavity 54 so that lymphatic fluid minus the separated fat is continuously provided to that cavity for reabsorption.

In all of the systems described heretofore the drainage lumen or conduit 34 is located within and extends through the venous system. As mentioned earlier and as should be reiterated herein that arrangement is not the only arrangement contemplated by this invention. Thus, for example, the drainage lumen 34 can be implanted subcutaneously between the thoracic duct and the abdomen, or any other place at which the reservoir/separator and associated valve/pump assembly are implanted.

It should also be pointed out at this juncture that the systems and methods of this invention need not make use of all of the components described heretofore. In this regard the reservoir/separator may be omitted from the system for various applications. Thus, for example in fat removal applications the system may merely comprise the drainage lumen and an implantable mechanism, e.g., a valve/pump assembly, coupled thereto to controllably drain the lymphatic fluid from the lymphatic system and provide the same to some portion of the being's body, e.g., the urinary bladder, for excretion of that fluid without effecting the separation of any components thereof prior to removal. In fact, in some applications the means for controllably draining the lymphatic fluid, e.g, the valve/pump assembly, may be located outside the body of the being.

Without further elaboration the foregoing will so fully illustrate my invention that others may, by applying current or future knowledge, adopt the same for use under various conditions of service.

I claim:

1. A method for effecting obesity control of a living being by removing at least one fat-like material from the lymphatic fluid flowing through the body of said living being, said fat-like material being selected from the group consisting of fats, cholesterols, phosphoglycerides, triglycerides, and lipoproteins, said method comprising coupling a first conduit to a duct within the body of said being having said lymphatic fluid flowing therethrough so that said lymphatic fluid flows into through said first conduit, whereupon said fat-like material within the lymphatic fluid is removed from the body of the being continually over a protracted period of time.

2. The method of claim 1 additionally comprising separating said at least one fat-like material from said lymphatic fluid and returning the remaining lymphatic fluid after separation of said at least one fat-like material therefrom to a first internal portion of the body of said being.

3. The method of claim 2 wherein said first internal portion of the body of said being comprises the peritoneum.

4. The method of claim 2 wherein said first internal portion of the body of said being comprises the gastro-intestinal tract.

5. The method of claim 2 wherein said first internal portion of the body of said being comprises the thoracic cavity.

6. The method of claim 2 wherein said first internal portion of the body of said being comprises the venous system.

7. The method of claim 2 wherein said remaining lymphatic fluid is provided to said first internal portion of the body of said being for reabsorption thereby on a continuous basis.

8. The method of claim 1 additionally comprising providing said separated fat to a second internal portion of the body of said being for excretion therefrom.

9. The method of claim 8 wherein said second internal portion of the body of said being comprises the urinary bladder.

10. The method of claim 1 wherein the fat is separated from said lymphatic fluid by gravity.

11. A method for removing at least one-fat like material from lymphatic fluid flowing through the body of a living being, said fat-like material being selected from the group consisting of fats, cholesterols, phosphoglycerides, triglycerides, and lipoproteins, said method comprising separating said at least one fat-like material from said lymphatic fluid flowing through the body of said living being and returning the remaining lymphatic fluid after separation of said at least one fat-like material therefrom to a first internal portion of the body of said being for reabsorption of said remaining lymphatic fluid by said body.

12. The method of claim 11 wherein said first internal portion of the body of said being comprises the peritoneum.

13. The method of claim 11 wherein said first internal portion of the body of said being comprises the gastrointestinal tract.

14. The method of claim 11 wherein said first internal portion of the body of said being comprises the thoracic cavity.

15. The method of claim 11 wherein said first internal portion of the body of said being comprises the venous system.

16. The method of claim 11 wherein said remaining lymphatic fluid is provided to said first internal portion of the body of said being for reabsorption thereby on a continuous basis.

17. A method for removing at least one predetermined material from the lymphatic fluid flowing through the body a living being continually over a protracted period of time, said method comprising extending a first conduit through the venous system of the being, coupling said first conduit to a duct within the body of said being having said lymphatic fluid flowing therethrough so that said lymphatic fluid flows into through said first conduit, and thereafter removing said at least one predetermined material from said lymphatic fluid via said first conduit continually over a protracted period of time.

18. The method of claim 17 wherein said first conduit is implanted subcutaneously.

19. A system for removing a first fat-like material from lymphatic fluid flowing through the body of a living being on a continual basis over a protracted period of time, said first fat-like material being selected from the group consisting of fats, cholesterols, phosphoglycerides, triglycerides, and lipoproteins, said system comprising first conduit means and reservoir means, said first conduit means being configured to be located within the body of said being coupled to a duct within the body of said being having said lymphatic fluid flowing therethrough so that said lymphatic fluid flows into said conduit means, said conduit means being coupled to said reservoir means for carrying said lymphatic fluid into said reservoir means, said reservoir means being operative for causing said fat-like material in said lymphatic fluid to be separated therefrom, whereupon said fat-like material is removed from the body of said being.

20. The system of claim 19 wherein said system additionally comprises second conduit means coupled to said reservoir means and to a first internal portion of the body of said being for carrying the lymphatic fluid remaining after the separation of said first material therefrom to said first internal portion for reabsorption by said first internal portion.

21. The system of claim 20 wherein said system additionally comprises third conduit means coupled to said reservoir means and to a second internal portion of the body of said being for carrying said first material after it has been separated from said lymphatic fluid to said second internal portion for excretion thereby.

22. The system of claim 19 wherein said system additionally comprises third conduit means coupled to said reservoir means and to a second internal portion of the body of said being for carrying said first material after it has been separated from said lymphatic fluid to said second internal portion for excretion thereby.

23. The system of claim 19 additionally comprising actuatable means located within the body of said being for causing said system to operate when said actuatable means is actuated and for causing said system to cease operating when said actuatable means is deactuated.

24. The system of claim 23 wherein said actuatable means is actuated and deactuated from outside of the body of said being.

25. The system of claim 24 wherein said actuatable means comprises pumping means.

26. The system of claim 24 wherein said actuatable means comprises valve means.

27. The system of claim 26 wherein said actuatable means comprises pumping means.

28. The system of claim 23 wherein said actuatable means comprises pumping means.

29. The system of claim 23 wherein said actuatable means comprises valve means.

30. The system of claim 29 wherein said actuatable means comprises pumping means.

31. The system of claim 23 wherein said system is implantable within the body of said being for disposition therein over a protracted period of time.

32. The system of claim 19 wherein said reservoir means is configured so that said first material is separated from said lymphatic fluid within said reservoir means by gravity.

33. The system of claim 26 wherein said system is implantable within the body of said being for disposition therein over a protracted period of time.

34. The system of claim 33 wherein said first conduit comprises an elongated member having a distal portion and a proximal portion, said elongated conduit being extendable through a portion of the vascular system of said so that said distal portion is in fluid communication with said duct and said proximal portion is in fluid communication with said reservoir means.

35. The system of claim 34 wherein said actuatable means is actuated and deactuated from outside of the body of said being.

36. The system of claim 35 wherein said actuatable means comprises pumping means.

37. The system of claim 35 wherein said actuatable means comprises valve means.

38. The system of claim 37 wherein said actuatable means comprises pumping means.

39. The system of claim 26 wherein said first conduit comprises an elongated flexible member having a distal portion and a proximal portion, said elongated flexible conduit being extendable through a portion of the vascular system of said so that said distal portion is in fluid communication with said duct and said proximal portion is in fluid communication with said reservoir means.

40. An implantable system for removing a first fat-like material from lymphatic fluid flowing through the body of a living being on a continual basis over a protracted period of time, said first fat-like material being selected from the group consisting of fats, cholesterols, phosphoglycerides, triglycerides, and lipoproteins, said system comprising first conduit means and control means, said first conduit means being configured to be located within the body of said being coupled to a duct within the body of said being having said lymphatic fluid flowing therethrough so that said lymphatic fluid flows into said conduit means, said conduit means being coupled to said control means, said control means being operative for causing said lymphatic fluid to be provided to means for removing said fat-like material from said lymphatic fluid and for discharging said fat-like material from the body of said being.

41. The system of claim 40 wherein said control means comprises an outlet coupled to a first internal portion of the body of said being so that said lymphatic fluid provided to said first internal portion of the body of said being is excreted therefrom.

42. The system of claim 41 wherein said control means comprises valve and pumping means.

43. The system of claim 40 wherein said control means comprises valve and pumping means.

44. The system of claim 40 wherein said first conduit means is arranged for extension through the venous system.

45. The system of claim 40 wherein said first conduit means is arranged for subcutaneous disposition within the body of said being.

46. An implantable system for controlling obesity in a living being by removing at least one fat-like material from the lymphatic fluid flowing through the body of said being, said at least one fat-like material being selected from the group consisting of fats, cholesterols, phosphoglycerides, triglycerides, and lipoproteins, said system comprising first conduit means configured to be located within the body of said being coupled to a duct within the body of said being having said lymphatic fluid flowing therethrough and also coupled to a first internal portion of the body of said being so that a controlled portion of said lymphatic fluid flows into said first conduit means to have said at least one fat-like material separated therefrom for removal from the being's lymphatic system, with at least a portion of said drained lymphatic fluid being provided to said first internal portion for reabsorption thereby.

47. The system of claim 46 wherein the amount of lymphatic fluid drained from said duct by said first conduit is controllable.

48. The system of claim 47 additionally comprising implantable control means coupled to said conduit for controlling the amount of lymphatic fluid drained from said duct by said first conduit means.

49. The system of claim 48 wherein said implantable control means comprises valve and pumping means.

50. A method for controlling obesity in a living being, said method comprising implanting first conduit means within the body of said being coupled so that said means is coupled to a duct within the body of said being having lymphatic fluid flowing therethrough and is also coupled to a first internal portion of the body of said being, draining a portion of said lymphatic fluid into said first conduit means from the being's lymphatic system, and providing at least a portion of said drained lymphatic fluid to said first internal portion for reabsorption thereby.

51. The method of claim 50 wherein the amount of lymphatic fluid drained from said duct by said first conduit means is controlled.

52. The method of claim 51 additionally comprising implanting control means within the body of said being, said control means being coupled to said first conduit means for controlling the amount of lymphatic fluid drained from said duct by said first conduit means.

53. The method of claim 52 wherein said implantable control means comprises valve and pumping means, and wherein said method comprises selectively operating said valve and pumping means.

54. The method of claim 50 wherein said first internal portion of the body of said being comprises the upper portion of the gastro-intestinal tract.

55. The method of claim 50 wherein said first internal portion of the body of said being comprises the peritoneum.

56. A system for removing a first predetermined material from the body of a living being on a continual basis over a protracted period of time, said system comprising first conduit means, reservoir means, and implantable control means, said first conduit means being configured to be located within the body of said being coupled to a duct within the body of said being having lymphatic fluid flowing therethrough so that said lymphatic fluid flows into said first conduit means, said first conduit means being coupled to said reservoir means for carrying said lymphatic fluid into said reservoir means, said reservoir means being operable to cause said first material in said lymphatic fluid to be separated therefrom. whereupon said first material is removed from the body of said being, said implantable control means being coupled to said first conduit means for controlling the amount of lymphatic fluid drained from said duct by said first conduit means.

57. The system of claim 56 wherein said implantable control means comprises valve and pumping means.

58. A method for withdrawing a portion of lymphatic fluid flowing through a duct within the body of a living being, said method comprising implanting first conduit means within the body of said being coupled so that said first conduit means is coupled to a duct within the body of said being having lymphatic fluid flowing therethrough and is also coupled to a first internal portion of the body of said being so that a portion of said lymphatic fluid is drained from said duct into said first conduit means, implanting control means within the body of said being, said control means being coupled to said first conduit means for controlling the amount of lymphatic fluid drained from said duct by said first conduit means, and providing at least a portion of said drained lymphatic fluid to said first internal portion for reabsorption thereby.

59. The method of claim 58 wherein said implantable control means comprises valve and pumping means, and wherein said method comprises selectively operating said valve and pumping means.

60. The method of claim 58 wherein said first internal portion of the body of said being comprises the upper portion of the gastro-intestinal tract.

61. The method of claim 58 wherein said first internal portion of the body of said being comprises the peritoneum.

62. A method for removing at least one fat-like material from the body of living being, said fat-like material being selected from the group consisting of fats, cholesterols, phosphoglycerides, triglycerides, and lipoproteins, said method comprising coupling a first conduit to a duct within the body of said being having lymphatic fluid flowing therethrough so that said fluid flows into and through said first conduit, whereupon said fat-like material within said lymphatic fluid is removed from the body of said being continually over a protracted period of time.

63. The method of claim 62 wherein said at least one fat-like material is removed from the body of said being continuously.

64. The method of claim 63 additionally comprising separating said at least one fat-like material from said lymphatic fluid and returning the remaining lymphatic fluid after separation of said at least one fat-like material therefrom to a first internal portion of the body of said being.

65. The method of claim 62 additionally comprising separating said at least one fat-like material from said lymphatic fluid and returning the remaining lymphatic fluid after separation of said at least one fat-like material therefrom to a first internal portion of the body of said being.

* * * * *